United States Patent [19]

Müller et al.

[11] Patent Number: 5,235,099
[45] Date of Patent: Aug. 10, 1993

[54] PROCESS FOR THE PREPARATION OF UREIDOPEROXYCARBOXYLIC ACIDS

[75] Inventors: Wolf-Dieter Müller, Hofheim am Taunus; Frank Jaekel, Kelkheim; Peter Naumann, Taunusstein; Gerd Reinhardt, Kelkheim, all of Fed. Rep. of Germany

[73] Assignee: Hoechst Aktiengesellschaft, Frankfurt am Main, Fed. Rep. of Germany

[21] Appl. No.: 793,815

[22] Filed: Nov. 18, 1991

[30] Foreign Application Priority Data

Nov. 16, 1990 [DE] Fed. Rep. of Germany ....... 4036646

[51] Int. Cl.$^5$ .................. C07C 407/00; C07C 409/40
[52] U.S. Cl. ............................................. 562/2; 562/6
[58] Field of Search ...................................... 562/2, 6

[56] References Cited

U.S. PATENT DOCUMENTS

| 4,634,551 | 1/1987 | Burns et al. .......................... 252/102 |
| 4,686,063 | 8/1987 | Burns ................................... 252/102 |
| 5,061,807 | 10/1991 | Gethoffer et al. ................... 548/473 |

FOREIGN PATENT DOCUMENTS 0349940 1/1990 European Pat. Off. .
6717087 6/1969 Netherlands .

Primary Examiner—José G. Dees
Assistant Examiner—Porfirio Nazario
Attorney, Agent, or Firm—Connolly and Hutz

[57] ABSTRACT

A process for the preparation of ureidoperoxycarboxylic acids of the formula

A─[NH─CO─NH─B─CO─OOH]$_x$, in which
x is the number 1 or 2,
A,
if x is 1,
is hydrogen, $C_1$-$C_{20}$-alkyl, aryl, preferably phenyl, or haloaryl, preferably chlorophenyl, or if x is 2,
is $C_1$-$C_{20}$-alkylene or arylene, preferably phenylene,
B is a group of the formula

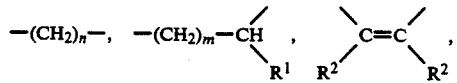

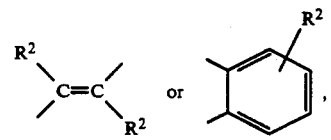

in which
n is a number from 1 to 20,
m is the number 0, 1 or 2,
$R^1$ is $C_1$-$C_{20}$-alkyl and
$R^2$ is in each case hydrogen or $C_1$-$C_{20}$-alkyl,
which comprises dissolving carbamoyllactams of the formula

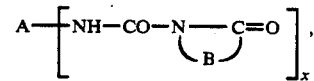

in which x, A and B have the abovementioned meanings, in a one- to six-fold, preferably a one- to three-fold, amount by weight of a strong catalyst acid, by then adding water in a one- to ten-fold molar excess, relative to the carbamoyllactam, to the solution of the carbamoyllactam in the catalyst acid and by heating the reaction mixture to form the ureidocarboxylic acid, by then adding to the reaction mixture an aqueous hydrogen peroxide solution in a one- to ten-fold, preferably a two- to four fold, molar excess per oxidizable carboxyl group of the ureidocarboxylic acid formed in the preceding reaction step, and by then precipitating the resulting ureidoperoxycarboxylic acid from the reaction mixture.

These compounds are suitable as bleaches, oxidants and disinfectants.

14 Claims, No Drawings

PROCESS FOR THE PREPARATION OF UREIDOPEROXYCARBOXYLIC ACIDS

DESCRIPTION

The present invention relates to a process for the preparation of ureidoperoxycarboxylic acids of the formula

A$[$NH—CO—NH—B—CO—OOH$]_x$, in which
x is the number 1 or 2,
A,
  if x is 1,
  is hydrogen, $C_1$-$C_{20}$-alkyl, aryl, preferably phenyl, or haloaryl, preferably chlorophenyl, or
  if x is 2,
  is $C_1$-$C_{20}$-alkylene or arylene, preferably phenylene,
B is a group of the formula

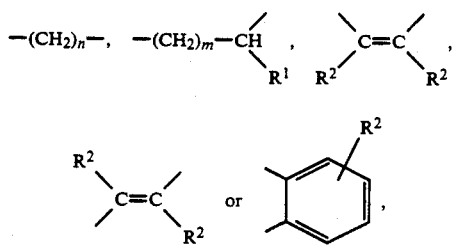

$-(CH_2)_n-$, $-(CH_2)_m-CH\begin{smallmatrix}R^1\\R^2\end{smallmatrix}$, $\begin{smallmatrix}\\\\\end{smallmatrix}C=C\begin{smallmatrix}\\R^2\end{smallmatrix}$ or in which
n is a number from 1 to 20,
m is the number 0, 1 or 2,
$R^1$ is $C_1$-$C_{20}$-alkyl and
$R^2$ is in each case hydrogen or $C_1$-$C_{20}$-alkyl.

Ureidoperoxycarboxylic acids are oxidants and can be used for bleaching textiles and for disinfection, in particular in sanitary installations, since their effect occurs at temperatures of 60° C. and below (German Patent Application P 40 16 980.4). The ureidoperoxycarboxylic acids, the precursors of the analogous peroxycarboxylic acids, can be prepared from an isocyanate and an ω-aminocarboxylic acid (German Patent Application P 40 16 980.4). Due to the process, one mol of salt is formed here per mol of ureidoperoxycarboxylic acid. The following oxidation to give the corresponding peracids is carried out as in EP-A-349,940.

Another process starts from isocyanates and lactams, from which carbamoyllactams are initially prepared. As masked isocyanates, carbamoyllactams per se are widely used and are available easily and economically (EP-A-10,766, EP-A-23,649 and BE-A-739,313). Opening of the lactam ring under basic conditions, for example with sodium hydroxide, inevitably leads to the undesired production of the salt and is therefore also unsuitable for large-scale use. However, cleavages with amines proceed unselectively and give product mixtures (Arch. Pharm. 320 (1987), 430). Opening of the lactam ring in the carbamoyllactam with sodium methylate is described in DE-A-3,504,967 and does proceed selectively, but of course with salt formation.

The present invention is based on the object of making available a process for the preparation of ureidoperoxycarboxylic acids which is ecologically acceptable and in which favorably priced starting materials can be employed.

It has surprisingly been found that the hydrolysis of the carbamoyllactams takes an unambiguous reaction course under acidic conditions and yields the ureidocarboxylic acids in high yield and purity. Moreover, these ureidocarboxylic acids can be oxidized with hydrogen peroxide directly under the reaction conditions used, i.e. in a one-pot reaction, to give the corresponding peracids.

The object is achieved by dissolving carbamoyllactams of the formula

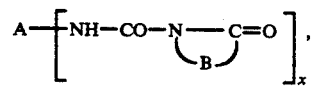

in which
x is the number 1 or 2,
A,
  if x is 1,
  is hydrogen, $C_1$-$C_{20}$-alkyl, aryl, preferably phenyl, or haloaryl, preferably chlorophenyl, or
  if x is 2,
  is $C_1$-$C_{20}$-alkylene or arylene, preferably phenylene
and
B is a group of the formula

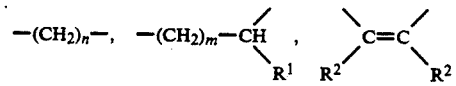

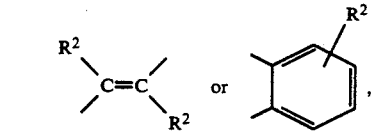

in which
n is a number from 1 to 20,
m is the number 0, 1 or 2,
$R^1$ is $C_1$-$C_{20}$-alkyl and
$R^2$ is in each case hydrogen or $C_1$-$C_{20}$-alkyl,
in a one- to six-fold, preferably a one- to three-fold, amount by weight of a strong catalyst acid, by then adding water in a one- to ten-fold molar excess, relative to the carbamoyllactam, to the solution of the carbamoyllactam in the catalyst acid and by heating the reaction mixture to form the ureidocarboxylic acid, by then adding to the reaction mixture an aqueous hydrogen peroxide solution in a one- to ten-fold molar excess per oxidizable carboxyl group of the ureidocarboxylic acid formed in the preceding reaction step, and by then precipitating the resulting ureidoperoxycarboxylic acid from the reaction mixture.

Strong catalyst acids used, for example, are sulfuric acid, methanesulfonic acid or an acidic ion exchanger. Preferably, sulfuric acid is employed as a 50 to 96% strength by weight, in particular as a 75 to 96% strength by weight, aqueous solution. Advantageously, the carbamoyllactam is initially dissolved in a one- to six-fold, preferably a one- to three-fold, amount by weight, relative to the carbamoyllactam, of catalyst acid. In order to open the lactam ring(s) of the carbamoyllactam by hydrolysis, water is added to the solution of the carbamoyllactam in the abovementioned catalyst acid in a one- to ten-fold, preferably a one- to three-fold, molar excess per lactam ring and the reaction mixture is heated for at least 10 minutes, preferably 10 to 120 minutes, in particular 30 to 80 minutes, at temperatures of at least 40° C., preferably 40° to 120° C., in particular 50 to 80° C.

The ureidocarboxylic acid formed from the reaction of the carbamoyllactam with acid and water can be oxidized directly in the present reaction mixture to fire the ureidoperoxycarboxylic acid, without it being necessary to isolate the ureidocarboxylic acid before the oxidation. For the oxidation, hydrogen peroxide is added to the reaction mixture in a one- to ten-fold, preferably two- to four-fold, molar excess per oxidizable carboxyl group of the ureidocarboxylic acid. Advantageously, hydrogen peroxide is used here as a 5 to 95% strength by weight, preferably 25 to 85% strength by weight, aqueous solution. The reaction temperature and reaction time for the oxidation depend on the stability of the resulting ureidoperoxycarboxylic acid. The reaction temperature is between −20° and +80° C., preferably between 5° and 60° C., in particular between 15° and 50° C., and the reaction time is between 15 and 180 minutes, preferably between 20 and 120 minutes.

The ureidoperoxycarboxylic acid in general precipitates out of the reaction mixture on addition of water and can be isolated by filtration or centrifugation. It is also possible to precipitate ureidoperoxycarboxylic acids which do not precipitate, or only incompletely precipitate, on addition of water by addition of aqueous solutions of basic salts.

The carbamoyllactams needed as starting materials for the process according to the invention can be prepared by known processes from an isocyanate of the formula A—[NCO]$_x$ and a lactam of the formula

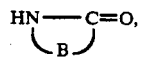

in which A, B and x have the abovementioned meanings, either in an organic solvent (EP-A-23,649 and DE-A-3,322,722) or without solvent (DE-A-3,143,060 and DE-A-3,536,017). Isocyanates used are preferably phenyl isocyanates, p-tolyl isocyanate, cyclohexyl isocyanate, octyl isocyanate and hexamethylene diisocyanate and lactams preferably used are laurolactam, ε-caprolactam and pyrrolidone.

The following ureidoperoxycarboxylic acids have proved advantageous for the purposes of the invention:
N-(N'-octylcarbamoyl)-6-aminoperoxyhexanoic acid,
N-(N'-cyclohexylcarbamoyl)-6-aminoperoxyhexanoic acid,
N-(N'-phenylcarbamoyl)-6-aminoperoxyhexanoic acid,
N-(N'-phenylcarbamoyl)-12-aminoperoxyundecanoic acid and
N,N'-bis(6-carbamoylperoxyhexanoic acid)-1,6-diaminohexane.

The advantages of the process according to the invention are the economical preparation of the ureidoperoxycarboxylic acids, the avoidance of production of salt caused by the process and the possibility of obtaining the ureidoperoxycarboxylic acids in a "one-pot reaction".

The ureidoperoxycarboxylic acids prepared according to the invention can be used as bleaches for textiles, as oxidants or as disinfectants, preferably in sanitary installations. For these purposes, they can be employed either in pure form or in appropriately formulated form, preferably as granules. For granulation, the processes described in EP-A-376,360, EP-A-273,334, EP-A-272,402 and EP-A-256,443 or those described in German Patent Applications P 40 11 185.7 and P 40 12 769.9 can be used.

The process according to the invention is illustrated in greater detail by the following examples.

EXAMPLE 1

Preparation of the Carbamoyllactams

The lactam (1 equiv.) is initially introduced and heated to 80° C. under an inert gas atmosphere. The appropriate isocyanate (1 equiv.) is then added dropwise in the course of 60 minutes at a temperature between 75 and 85° C. The reaction mixture is then stirred between 120 and 130° C. for a further 3 hours and, for crystallization, poured onto a metal plate. The yields are quantitative and the compounds obtained can usually be directly reacted further.

With laurolactam, the reaction is carried out in boiling xylene, the isocyanate being added dropwise to the solution of the lactam. The reaction time is 8 hours.

EXAMPLE 2

N'(N'-phenylcarbamoyl)-6-aminoperoxyhexanoic acid 23.2 g (0.1 mol) of N-(N'-phenylcarbamoyl)-2-oxoazepane are dissolved in a mixture of 50.0 g of sulfuric acid (96% strength by weight) and 3.6 g (0.2 mol) of water and heated at 60° C. for 40 minutes. After cooling to 15° C., 29.2 g (0.3 mol) of hydrogen peroxide (35% strength by weight) are added dropwise such that the internal temperature does not exceed 15° C. The reaction mixture is stirred between 15° and 20° C., with cooling, for a further 60 minutes and 100 ml of water are then added. The precipitated peroxycarboxylic acid is filtered off with suction and the filter cake is washed free of mineral acid with water and dried at 40° C. in a water pump vacuum.

Yield: 25.6 g (96.2%)
Active oxygen content: 5.81% (96.8%)
m.p.: 102° C.

EXAMPLE 3

N-(N'-phenylcarbamoyl)-12-aminoperoxydodecanoic acid 31.6 g (0.1 mol) of N-phenylcarbamoyllaurolactam are dissolved in 50.0 g of methanesulfonic acid (98% strength by weight), 3.6 g (0.2 mol) of water are added and the mixture is heated at 80° C. for 30 minutes. After cooling the reaction mixture to 25° C., 17.0 g (0.25 mol) of hydrogen peroxide (50% strength by weight) are added dropwise such that the internal temperature can be kept between 22 and 25° C. After stirring at 25° C. for 20 minutes, 100 ml of water are added and the precipitated peroxycarboxylic acid is filtered off with suction. The filter cake is washed free of mineral acid with water and dried at 40° C. in a water pump vacuum.

Yield: 34.2 g (97.7%)
Active oxygen content: 4.24% (93%)
m.p.: 116° C.

EXAMPLE 4

N-(N'-cyclohexylcarbamoyl)-6-aminoperoxyhexanoic acid 23.7 g (0.1 mol) of N-(N,-cyclohexylcarbamoyl)-2-oxoazepane are dissolved in 50.0 g of sulfuric acid (96% strength by weight), 3.6 g (0.2 mol) of water are added and the mixture is heated at 80° C. for 30 minutes. After cooling the reaction mixture to 25° C., 20.4 g (0.3 mol) of hydrogen peroxide (50% strength by weight) are added dropwise such that the internal temperature does not exceed 25° C. After stirring at room temperature for 30 minutes, 100 ml of water are added to the mixture with ice-cooling and the precipitated peroxycarboxylic acid is filtered off with suction. The filter cake is washed free of mineral acid with water and dried at 40° C. in a water pump vacuum.

Yield: 23.5 g (86.4%)
Active oxygen content: 5.3 % (89.8%)
m.p.: 125°–128° C.

EXAMPLE 5

N-(N'-octylcarbamoyl)-6-aminoperoxyhexanoic acid 26.8 g (0.1 mol) of N-(N,-octylcarbamoyl)-2-oxoazepane, 50.0 g of sulfuric acid (96% strength by weight) and 3.6 g (0.2 mol) of water are heated at 80° C. for 30 minutes and the mixture is then reacted with 20.4 g (0.3 mol) of hydrogen peroxide (50% strength by weight) for 30 minutes at 15° C. as described in Example 4 and worked up.

Yield: 29.4 g (97.3%)
Active oxygen content: 5.04% (95.3%)
m.p.: 76°–77° C.

EXAMPLE 6

N,N'-bis(6-carbamoylperoxyhexanoyl)-1,6-diaminohexane 39.4 g (0.1 mol) of N,N'-bis(2-oxoazepane-1-carbonyl)hexanediyldiamine, 50.0 g of sulfuric acid (96% strength by weight) and 7.2 g (0.4 mol) of water are heated at 80° C. for 30 minutes and the mixture is then reacted with 34.0 g (0.5 mol) of hydrogen peroxide (50% strength by weight) for 30 minutes between 25 and 30° C. as described in Example 4 and worked up.

Yield: 43.5 g (94.2%)
Active oxygen content: 5.2 % (75%)
m.p.: 155° C.

We claim:

1. A process for the preparation of a ureidoperoxycarboxylic acid of the formula A⁅NH—CO—NH—B—CO—OOH]$_x$, in which
x is the number 1 or 2,
A,
   if x is 1,
   is hydrogen, $C_1$–$C_{20}$-alkyl, aryl, or haloaryl, or
   if x is 2,
   is $C_1$–$C_{20}$-alkylene or arylene,
B is a group of the formula

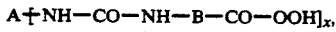

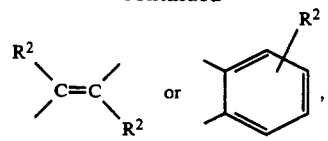

in which
n is a number from 1 to 20,
m is the number 0, 1 or 2,
$R^1$ is $C_1$–$C_{20}$-alkyl and
$R^2$ is in each case hydrogen or $C_1$–$C_{20}$-alkyl
which comprises dissolving carbamoyllactams of the formula

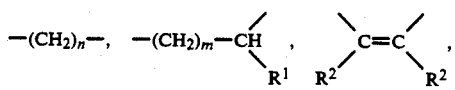

in which x, A and B have the abovementioned means, in a one- to six-fold, amount by weight of a strong catalyst acid, by then adding water in a one- to tenfold molar excess, relative to the carbamoyllactam, to the solution of the carbamoyllactam in the catalyst acid and by heating the reaction mixture to form the ureidocarboxylic acid, by then adding to the reaction mixture an aqueous hydrogen peroxide solution in a one- to ten-fold, molar excess per oxidizable carboxyl group of the ureidocarboxylic acid formed in the preceding reaction step, and by then precipitating the resulting ureidoperoxycarboxylic acid from the reaction mixture.

2. The process as claimed in claim 1, wherein sulfuric acid, methanesulfonic acid or an acidic ion exchanger is used as the strong catalyst acid.

3. The process as claimed in claim 2, wherein a 50 to, aqueous sulfuric acid solution is employed as the strong catalyst acid.

4. The process as claimed in claim 1, wherein an 80 to 98% strength by weight methanesulfonic acid is used as the strong catalyst acid.

5. The process as claimed in claim 1, wherein water is added to the solution of the carbamoyllactam in the catalyst acid in a one- to three-fold molar excess, relative to the carbamoyllactam.

6. The process as claimed in claim 1, wherein the reaction mixture composed of the carbamoyllactam, the catalyst acid and water is heated to at least 40° C. for at least 10 minutes.

7. The process as claimed in claim 1, wherein hydrogen peroxide is added to the reaction mixture as a 5 to 95% strength by weight aqueous solution.

8. The process as claimed in claim 1, wherein hydrogen peroxide is allowed to act on the reaction mixture containing the ureidocarboxylic acid for at least 15 minutes.

9. A process as claimed in claim 1, wherein A, if x is 1, is phenyl or chlorophenyl.

10. A process as claimed in claim 1, wherein A, if x is 2, is phenylene.

11. A process as claimed in claim 1, wherein said aqueous hydrogen peroxide solution is added to the reaction mixture in a two- to four-fold.

12. A process as claimed in claim 2, wherein a 75 to 96% strength by weight sulfuric acid solution is employed as the strong catalyst acid.

13. The process as claimed in claim 1, wherein dissolving carbamoyllactams is in a one- to three-fold amount by weight of a strong catalyst acid.

14. The process as claimed in claim 1, wherein the ureidoperoxycarboxylic acid obtained is incorporated into granules for use as a bleach, oxidant or disinfectant.

* * * * *